(12) United States Patent
Haerizadeh et al.

(10) Patent No.: US 9,018,013 B2
(45) Date of Patent: Apr. 28, 2015

(54) MOLECULAR BIOLOGY TOOLS FOR ALGAL ENGINEERING

(75) Inventors: Farzad Haerizadeh, San Diego, CA (US); Todd Peterson, Coronado, CA (US); Wen Chen, Carslbad, CA (US); Ewa Lis, Lakeside, CA (US)

(73) Assignee: Life Technologies Corporation, Carlsbad, CA (US)

( * ) Notice: Subject to any disclaimer, the term of this patent is extended or adjusted under 35 U.S.C. 154(b) by 95 days.

(21) Appl. No.: 13/584,615

(22) Filed: Aug. 13, 2012

(65) Prior Publication Data

US 2013/0065313 A1 Mar. 14, 2013

Related U.S. Application Data

(60) Provisional application No. 61/523,138, filed on Aug. 12, 2011.

(51) Int. Cl.
| | |
|---|---|
| *C12N 1/00* | (2006.01) |
| *C12N 1/12* | (2006.01) |
| *C12N 13/00* | (2006.01) |
| *C12N 15/00* | (2006.01) |
| *C12N 5/00* | (2006.01) |
| *C12N 15/87* | (2006.01) |
| *C12N 15/79* | (2006.01) |
| *C12N 15/82* | (2006.01) |

(52) U.S. Cl.
CPC .............. *C12N 5/0025* (2013.01); *C12N 15/87* (2013.01); *C12N 15/79* (2013.01); *C12N 15/8206* (2013.01)

(58) Field of Classification Search
CPC .......... C12N 1/00; C12N 13/00; C12N 15/00; C12N 15/09; C12N 15/8201; C12N 15/8202; C12N 15/8206; C12N 15/8209; C12N 15/8213; C12N 15/8214; C12N 2510/00; C12N 2529/00
See application file for complete search history.

(56) References Cited

U.S. PATENT DOCUMENTS

| | | | |
|---|---|---|---|
| 8,119,859 B2 | 2/2012 | Vick et al. | |
| 2009/0011480 A1* | 1/2009 | Trimbur et al. | ............... 435/134 |

FOREIGN PATENT DOCUMENTS

CN 101736025 6/2010

OTHER PUBLICATIONS

Heath (Plant Physiol.1977. vol. 59;911-914).*
Chimiklis et al., (Plant Science Letters. 1976. vol. 6;97-102).*
Gonzalez-Ballester et al., "Reverse genetics in *Chlamydomonas*: a platform for isolating insertional mutants", *Plant Methods*, vol. 7, No. 1, Jul. 27, 2011, 24.
International Application No. PCT/US2012/050628, International Search Report and Written Opinion, Jun. 14, 2013.
Ladygin et al., "Efficient transformation of mutant cells of *Chlamydomonas reinhardtii* by electroporation", *Process Biochemistry*, vol. 39, No. 11, Jul. 1, 2004, 1685-1691.
Shimogawara et al., "High-Efficiency Transformation of *Chlamhydomonas reinhardtii* by Electroporation", *Genetics*. vol. 148, No. 4, Apr. 1, 1998, 1821-1828.

* cited by examiner

*Primary Examiner* — Ja'na Hines

(57) ABSTRACT

The present invention provides compositions and methods for the genetic manipulation of Algal cells. The compositions and methods allow enhanced transfer of genetic material into Algal cells and the cloning and selection of genetically modified cells. Expression of proteins encoded by the genetic material will be enhanced by the methods and compositions of the invention.

5 Claims, 3 Drawing Sheets

MOLECULAR BIOLOGY TOOLS FOR ALGAL ENGINEERING

CROSS REFERENCE TO RELATED APPLICATIONS

This application claims the benefit of priority of U.S. Provisional Application No. 61/523,138, filed Aug. 12, 2011 which is hereby incorporated by reference in its entirety.

FIELD OF THE INVENTION

This invention relates generally to the field of algal cell biology. More specifically, it relates to compositions and methods of cloning and expressing nucleic acids molecules in Algae.

BACKGROUND

Algal biotechnology has strong potential to solve pressing challenges relating to the availability of food, renewable energy and climate change. Yet the tools for algal biotechnology do not currently allow for swift adoption of the organisms for synthetic biology applications. Main areas of research that need attention are: high level transgene expression, targeted integration, homologous recombination, elimination of silencing, ability to efficiently deliver large sections of heterologous DNA as well as robust tools for production organisms. Methods and compositions delineated below seek to address these challenges thru commercialization of advanced synthetic biology toolkits for algal hosts.

SUMMARY

The present invention provides nucleic acids, vectors, plasmids, host cells, buffers and methods for cloning genes and expressing proteins in algal cells. These methods and compositions provide a collection of tools for manipulating the genome of an algal cell and cloning and selection of desired strains so that a high level expression of genes of interest may be obtained. Some embodiments provide for a composition for transformation of an algal cell with DNA the composition comprising one or more sugars, and a biological buffer. In particular embodiments the one or more sugars are selected from the group consisting of sucrose, fructose, maltose, trehalose, sorbitol, maltitol, erythrytol, mannitol, xylose, raffilose and lactose. In further embodiments the one or more sugars are present at a total concentration of from 40 mM to 100 mM. For other embodiments the biological buffer is selected from the group consisting of Bis-Tris Propane, TRIS, AMPD, TABS, AMPSO, CHES and CAPSO and in other embodiments the concentration of the biological buffer is from 5 mM to 100 mM and may have a pH from 8 to 10. Some embodiments provide for an isolated nucleic acid which exhibits promoter activity in an algal cell. Another embodiment may be an algal cell comprising an isolated nucleic acid sequence which exhibits promoter activity. Further embodiments may be methods for performing homologous recombination in an algal cell comprising co-transforming the algal cell with a protein that enhances homologous recombination. Other embodiments may provide for a cyanobacteria derived from cyanobacteria strain BC104 comprising one or more resistance markers and one or more promoters. A further embodiment may be a plasmid comprising an origin of replication and plasmid maintenance regions derived from pANL. Another embodiment may be an algal cell large capacity vector capable of replicating in *Chlorella*. A further embodiment may be an algal cell comprising an isolated nucleic acid which encodes an RNA polymerase under the control of an inducible promoter the isolated nucleic acid further comprising a reporter gene under control by the same inducible promoter.

DETAILED DESCRIPTION

Figure 1:
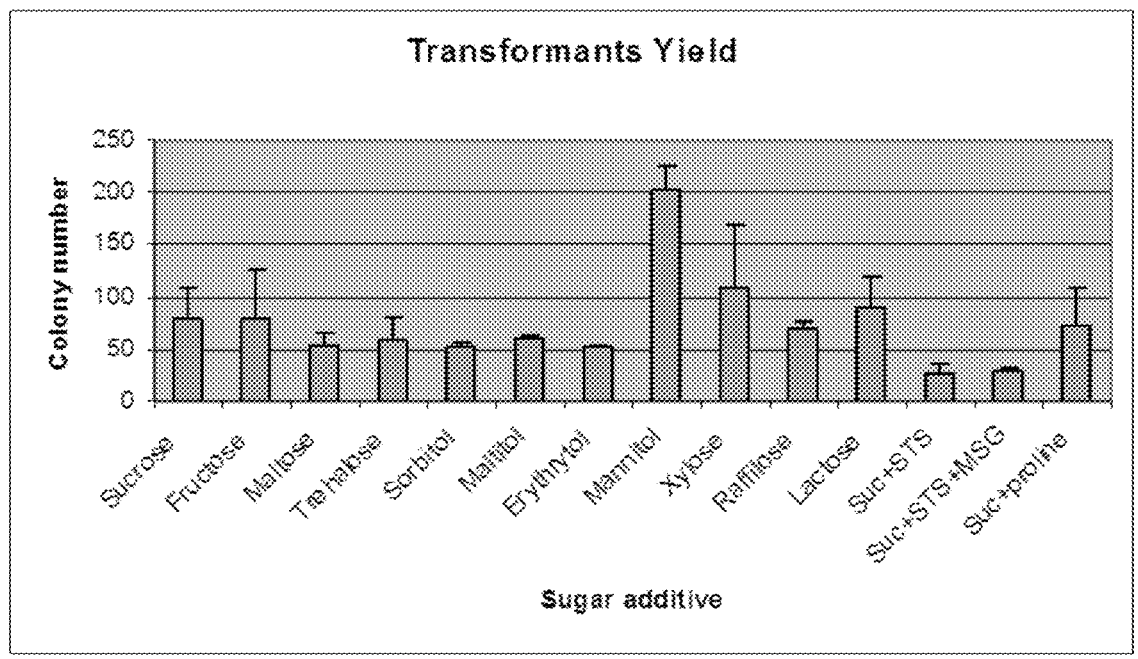
FIG. 1 shows the yield of transformants when different sugars are used in the transformation buffer.

Algae or algal cell, refer to plants or cells belonging to the subphylum Algae of the phylum Thallophyta. The algae are unicellular, photosynthetic, oxygenic algae and are non-parasitic plants without roots, stems or leaves; they contain chlorophyll and have a great variety in size, from microscopic to large seaweeds. Green algae, belonging to Eukaryota-Viridiplantae-Chlorophyta-Chlorophyceae, can be used. Blue-green, red, or brown algae may also be used. Exemplary algae for which the methods and reagents described herein may be used include those of the genus *Chlamydomonas* and the genus *Chlorella*.

Cyanobacteria are photosynthetic bacteria which require light, inorganic elements, nitrogen sources, water and a carbon source, generally $CO_2$, to metabolize and grow. Cyanobacteria are photosynthetic prokaryotes which carry out oxygenic photosynthesis. The main product of the metabolic pathway of Cyanobacteria during aerobic conditions is oxygen and carbohydrates. Exemplary cyanobacteria include those found in Donald Bryant, The Molecular Biology of Cyanobacteria, published by Kluwer Academic Publishers (1994). Representative examples include *Synechococcus* such as *Synechococcus lividus* and *Synechococcus elongatus*; and *Synechocystis* such as *Synechocystis minervae*, such as *Synchocystis* Sp PCC 6803.

Nucleic acid: As used herein, a nucleic acid is a sequence of contiguous nucleotides (riboNTPs, dNTPs or ddNTPs, or combinations thereof) of any length, which may encode a full-length polypeptide or a fragment of any length thereof, or which may be non-coding. As used herein, the terms "nucleic acid molecule" and "polynucleotide" may be used interchangeably.

Transformation is a process for introducing heterologous DNA into a plant cell, plant tissue, or plant. Transformed plant cells, plant tissue, or plants are understood to encompass not only the end product of a transformation process, but also transgenic progeny thereof.

Transformed, transgenic, and recombinant refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof.

Promoter: As used herein, a promoter is an example of a transcriptional regulatory sequence, and is specifically a nucleic acid sequence generally described as the 5'-region of a gene located proximal to the start codon. The transcription of an adjacent nucleic acid segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

A gene that is codon-optimized for expression in an organism is a gene whose nucleotide sequence has been altered with respect to the original nucleotide sequence, such that one or more codons of the nucleotide sequence has been changed to a different codon that encodes the same amino acid, in which the new codon is used more frequently in genes of the organism of interest than the original codon. The degeneracy of the genetic code provides that all amino acids except form methionine and tryptophan are encoded by more than one codon. For example, arginine, leucine, and serine are encoded by different six different codons; glycine, alanine, valine, threonine, and proline are encoded by four different codons. Many organisms use certain codons to encode a particular amino acid more frequently than others. Thus, for adequate or optimal levels of expression of an encoded protein, a gene may be codon-optimized to change one or more codons to new codons (preferred codons) that are among those used more frequently in the genes of the host organism (referred to as the codon preference of the organism). As used herein, a codon-optimized gene or nucleic acid molecule of the invention need not have every codon altered to conform to the codon preference of the intended host organism, nor is it required that altered codons of a codon-optimized gene or nucleic acid molecule be changed to the most prevalent codon used by the organism of interest. For example, a codon-optimized gene may have one or more codons changed to codons that are used more frequently that the original codon (s), whether or not they are used most frequently in the organism to encode a particular amino acid.

Algal Transformation Reagent

The transformation efficiency in *Chlamydomonas* using conventional transformation reagents and procedures is extremely low and may limit the use of this organism for high throughput applications such as testing libraries of evolved proteins or libraries of cDNAs from other organisms. To address this issue we have developed an optimized transformation buffer and corresponding optimized electroporation conditions using the Neon® (Life Technologies, Carlsbad, Calif.) and Bio-Rad Genepulse® II (BioRad, Hercules, Calif.) electroporation apparatus.

The transformation buffer may be comprised of one or more sugars and a buffer salt to regulate pH. Suitable sugars include but are not limited to sucrose, fructose, maltose, trehalose, sorbitol, maltitol, erythrytol, mannitol, xylose, raffilose and lactose. The total sugar concentration may be from 40 mM to 100 mM, 50 mM to 100 mM, 60 mM to 100 mM, 70 mM to 100 mM, 40 mM to 90 mM, 40 mM to 80 mM, 40 mM to 70 mM or 40 mM to 60 mM. When more than one sugar is used the concentration of any one sugar may be from 10 mM to 100 mM.

The pH of the transformation buffer may be from pH 7 to pH 10, pH 8 to pH 10, pH 9 to pH 10, pH 7 to pH 9 or pH 7 to pH 8. A number of Biological Buffers suitable for this pH range are available from Sigma-Aldrich (St. Louis, Mo.) including, but not limited to, Bis-Tris Propane, TRIS, AMPD, TABS, AMPSO, CHES and CAPSO. The concentration of the buffer may be from 5 mM to 100 mM, 5 mM to 90 mM, 5 mM to 80 mM, 5 mM to 70 mM, 5 mM to 60 mM, 5 mM to 50 mM, 10 mM to 100 mM, 20 mM to 100 mM, 30 mM to 100 mM, 40 mM to 100 mM or 50 mM to 100 mM.

Identification of Strong Promoters for Eukaryotic Algae.

Large DNA viruses that infect *Chlorella* have been used in the past as a source of strong promoters that have been applied to biotechnological applications in plants and bacteria. With the emergence of algal biotechnology, the isolation of these promoters for algal vector development holds even greater promise. Previously, viral genomes were panned for highly active promoters in a high-throughput manner by generating a library of randomly sheared fragments of the >300 kb viral genomes. Several strong promoters were isolated that function in plants. Since there are many different *Chlorella* isolates and many large DNA algal viruses, the possibility of isolating a wide range of promoters that have a myriad of useful qualities exist. These large DNA viruses employ a wide range of DNA methylation patterns suggesting that they may have varying degrees of resistance to gene silencing due to DNA methylation when used in vectors.

To identify the viral promoters with varying and useful qualities, viral genomes may be sheared or cleaved by a unique *Chlorella* virus encoded restriction endonuclease. Each fragment may then be cloned into a bidirectional reporter vector and screened. Ideally, reporters that are amenable to FACS sorting such as GFP will be used. Strong promoters will be isolated and validated with additional reporter genes. Candidate promoters will also be evaluated for maintenance of expression as a function of culture time to address silencing.

Development of Genetic Tools for Algal Production Strain—*Chlorella*.

*Chlorella* is a widely used platform organism in algal biotechnology with well established mass culture. It is typically grown for consumption as a health supplement or animal feed due to its high protein content as well as high levels of polyunsaturated fatty acids. *Chlorella* is also now increasingly used for biofuels research due to its high lipid content as well as ability for many strains to grow under heterotrophic conditions.

Initial reports show that genetic manipulation of *Chlorella* is feasible however the tools for this organism are in their infancy.

Functional *chlorella* viral promoter elements will be evaluated in a selected set of *Chlorella* strains such as: *C. vulgaris, C. protothecoides, C. pyrenoidosa, C. ellipsoidea*. Reporter gene expression from the promoters may be tested together with evaluation of common resistance markers such as hygromycin and their optimization for use in *Chlorella*. Development of additional resistance markers with mass culture potential such as glyphosate resistance may be of value as well. Lastly feasibility of performing targeted integration in *Chlorella* will be established.

Enable Homologous Recombination in Eukaryotic Algae.

Targeted integration can alleviate the need for screening large numbers of clones and can generally result in more uniform expression levels across different clones however it does not address the inability to disrupt genes in green algae in a targeted fashion. The need still exists for homologous recombination driven gene disruption to enable quick generation of e.g. deletion mutants or promoter replacements in the nuclear genome.

Homologous recombination between the organism's genome and introduced DNA has been shown to occur in many organisms including yeast and mammalian cells, but remains difficult in photosynthetic organisms. Nevertheless homologous recombination does occur in *Chlamydomonas* nuclear genome albeit at a low frequency. Specifically, the NIT8 locus has been used to deliver a selectable marker, CRY1-1 that confers emetine resistance, via homologous recombination. Disruption of NIT8 results in chlorate resistance thus allowing for selection of transformants that disrupted this locus. Following selection with both chlorate and emetine, a construct containing 8.2 kb of homology and designed to disrupt NIT8 with CRY1-1 was found to correctly disrupt the locus in only 1/2000 transformants. Strategies to increase the rate of homologous recombination may include: co-transformation with RecA or other proteins such as eukaryotic Rad51 homologs, evaluation of factors that affect recombination efficiency (e.g. DNA amount, length of homology, electroporation conditions, cell culture conditions), use of DNA single or double strand break agents or irradiation, as well as effects of cell cycle.

Highly efficient homologous recombination does occur in the *Chlamydomonas* chloroplast. Characterization of genes that facilitate this process in the chloroplast given its' small size appears feasible with consequent expression of them in the nucleus and re-evaluation of efficiency of nuclear homologous recombination.

Improvement of Genetic Tools for a Cyanobacterial Production Strain.

Cyanobacteria have several traits that make them attractive production hosts. They have a wide range of metabolic capabilities while having little nutritional requirements. Some cyanobacteria not only fix carbon dioxide but also fix nitrogen reducing the need for fertilizer. They can tolerate high pH, high light intensity (including protection from UV light) and often high salt—traits that offer crop protection. Many cyanobacteria also produce mucilaginous envelope that protects them against predators and/or desiccation. Most importantly, cyanobacteria being prokaryotic are easy to manipulate genetically and offer advantages of cistronic expression as well as small genomes that can be more easily characterized—important traits for synthetic biology hosts.

Strain BC104 (or BL0902) was isolated in Imperial Valley, Calif. and developed as a production strain due to presence of many favorable traits. BC104 belongs to the *Leptolyngbya* sp., is filamentous, shows robust growth in 20-40° C. temperature range, can tolerate high pH (pH 11) and urea (used for predator control), grows in up to 0.5M salt (sea water concentration) and tolerates high solar irradiance. The growth rate of BC104 exceeds that of Spirulina in laboratory culture and is on par with Spirulina outdoors with excellent culture stability. BC104 can also be harvested using similar screening methods used for Spirulina. BC104 has been shown to accumulate >25% fatty acids/dry cell weight following conversion to FAME. In addition to these desirable qualities, BC104 is amenable to transformation that is reliable, efficient, and stable. Transformation may be demonstrated by the introduction of a plasmid that encodes yemGFP on RSF1010 broad host range origin plasmid by conjugation.

Whereas the production traits of BC104 have been well characterized, the genetic tool box for this strain is still rather small. Further development of the tools will require a set of robust resistance markers, evaluation of additional promoters, demonstration of expression of non-reporter genes that are relevant biotechnologically as well as demonstration of gene knockouts via homologous recombination. Moreover, the organism's genome will be sequenced and annotated.

Development of High Capacity Gene Transfer System for Cyanobacteria.

There are several methods for DNA delivery into cyanobacteria, the most prevalent being conjugation and natural transformation. Natural transformation has the advantage of ease of use but is limited to few model organisms such as *Synechococcus elongatus* and *Synechocystis*. Conjugation is more widely used and has many advantages such as high efficiency of DNA transfer, low species selectivity and capacity to transfer very large DNA segments with limits typically imposed by the recipient organism rather than transfer capacity. Conjugation from *E. coli* has been successfully used to deliver DNA to many cyanobacterial species such as: *Synechococcus elongatus* PCC7942, *Anabaena* PCC7120, *Nostoc punctiforme* ATCC 29133, *Cyanothece* sp. ATCC 51142, *Synechococcus* sp. WH8102, *Chroococcidiopsis* sp. *Tolypothrix* sp. PCC7601.

Given robust high capacity DNA transfer mechanisms, next step is establishment of a universal plasmid or small subset of plasmids with broad host range specificity. A good candidate for origin of replication is based on RSF1010 plasmids (oriV, mob, rep) which has been shown to replicate, albeit with poor efficiency in some cases, in distant species of cyanobacteria: *Synechococcus elongatus* PCC7942, *Synechocystis* PCC6803, *Synechocystis* PCC6714, *Anabaena* PCC7120, *Cyanothece* sp. ATCC 51142, *Leptolyngbya* sp. BL0902 (BC104). Improvement of host range specificity in addition to replication efficiency in cyanobacteria can be done by sequential mutagenesis and selection in a group of cyanobacterial strains of interest.

RSF1010 appears to have poor stability in *Synechococcus elongatus* PCC7942. Development of the large endogenous plasmid pANL for high capacity cloning may prove to be a more short term solution for this platform organism. pANL is 46 kb in length, 53% GC content and encodes 58 orfs. There are 4 structural and functional regions that have been characterized: the replication origin region, signal transduction region, plasmid maintenance region (containing a toxin-antitoxin addition cassette) and sulfur-regulated region. Both replication origin and plasmid maintenance regions are required for persistance of pANL in the cells.

To enable high capacity cloning in *Synechococcus elongatus*, the replication origin and plasmid maintenance origins from pANL will first be minimized in size while maintaining functionality and then combined with yeast elements to allow high order assembly as well as elements to enable conjugation from *E. coli* if necessary. The hybrid vector will be evaluated for stability as well as DNA carrying capacity.

Development of Viral Gene Transfer System for High Capacity Cloning in Green Algae.

An important application of algae genetic engineering tools would be the development of an easily useable and reliable viral vector for gene delivery and integration. A wide variety of viral vectors exist for mammalian cell systems and *agrobacterium* provide an extremely versatile and powerful system in plants. While recombinant manipulation and subsequent transformation of algae hosts with the large DNA algal viruses has proven elusive to date, the potential for developing these viruses as vectors is strong.

Initial efforts in the development of large capacity viral delivery system for eukaryotic algae may focus on large *chlorella* viruses such as the PBCV-1 virus and their host *Chlorella* NC64A with key aspect of understanding and controlling lysis vs lysogeny of the virus. Several approaches may be necessary to identify the lysis genes such as transcriptome analysis of early, middle and late expressed genes during infection in concert with bioinformatics analysis of gene candidates. A high throughput approach of transposon mutagenesis of viral particles and screening for infection but lack of lysis may be tried. Understanding the mechanisms of lysis may not only be valuable from the standpoint of engineering a gene delivery method but also from discovering methods to engineer inducible lysis for product separation approaches.

In addition to identification of lysis genes, the capacity to introduce and carry exogenous DNA will need to be evaluated with concomitant genome streamlining of the virus to increase that capacity.

Development of *Chlamydomonas* T7 RNA pol/T7 Promoter Chloroplast Expression Platform.

T7 RNA polymerase is an RNA polymerase from T7 bacteriophage with extremely high specificity towards the T7 promoter, high processivity and low error rate. T7 RNA polymerase is commonly used in *E. coli* expression platforms (e.g. BL21 DE3) and has been successfully applied to drive expression from the T7 promoter in several organisms including: *S. cerevisiae* mitochondria, *E. coli*, *Bacillus megaterium* and *Pseudomonas*. Recently the Voigt lab at UCSF has developed variants of T7 RNA polymerases with altered processivity and specificity as well as a suite of T7 promoters of different strength.

Given the demonstration that T7 RNA polymerase system can be used in yeast mitochondria as well as the prokaryotic nature of chloroplast expression machinery, it should be feasible to apply the T7 RNA polymerase/T7 promoter system to express genes in the chloroplast. Both wild-type T7 RNA polymerase as well as the low processivity (Voigt lab) T7 RNA polymerase (codon optimized for chloroplast expression) will be evaluated. The polymerase may be placed under control of an inducible promoter to enable regulated levels of expression. A reporter gene such as GFP may be placed under control of the T7 promoter and the expression of GFP following induction of T7 RNA polymerase will be evaluated.

EXAMPLE 1

Transformation Yield with Transformation Buffers Having Different Sugar Compositions Wild type *Chlamydomonas reinhardtii* cells were washed twice with 2.5 ml of an electroporation buffer comprising 40 mM of the selected sugar, and 10 mm Tris adjusted to a pH of 7.4. After washing, the cells were resuspended in the electroporation buffer at a concentration of $2 \times 10^8$ cells/ml. For each electroporation reaction, 250 µl cells were mixed with 2 µg of V1-Gus-ScaI linear DNA and incubated at 4° C. for 5 min. Immediately before electroporation the reaction mixture was transferred to a pre-chilled cuvette and then electroporation performed in a Bio-Rad Genepulser® II apparatus with settings of 500V, 50 mF and 800 W. The reactions were set on the bench for 15 min for resting and then transferred into 10 ml of TAP media with 40 mM sucrose to recover over night with light. Transformation efficiency was determined by plating 1/100 of each reaction. The results are shown in FIG. 1.

EXAMPLE 2

Transformation Yield with Transformation Buffers Having Different pH

Figure 2:
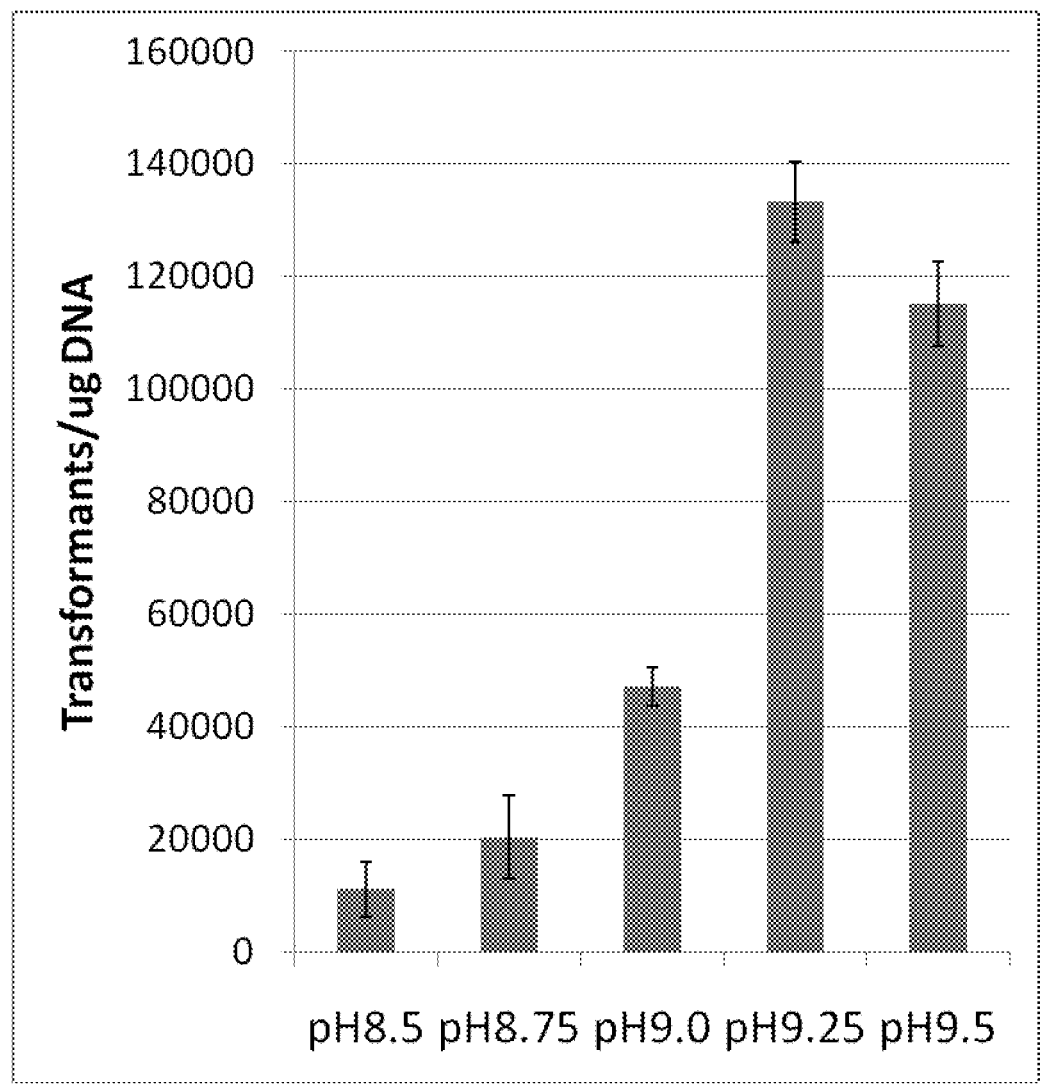
FIG. 2 shows the transformation efficiency when using the optimized transformation buffer at different pH.

Wild type *Chlamydomonas reinhardtii* cells were washed twice with 2.5 ml of an electroporation buffer comprising 40 mM sucrose, 10 mM sorbitol and 10 mm CHES adjusted to a pH of between 8.5 and 9.5. After washing, the cells were resuspended in the electroporation buffer at a concentration of $2 \times 10^8$ cells/ml. For each electroporation reaction, 250 µl cells were mixed with 2 µg of V1-Gus-ScaI linear DNA and incubated at 4° C. for 5 min. Immediately before electroporation the reaction mixture was transferred to pre-chilled cuvettes and then electroporation performed in a Bio-Rad Genepulser® II apparatus with settings of 500V, 50 mF and 800 W. The reactions were set on the bench for 15 min for resting and then transferred into 10 ml of TAP media with 40 mM sucrose to recover over night with light. Transformation efficiency was determined by plating 1/100 of each reaction. The results are shown in FIG. 2.

EXAMPLE 3

Transformation Yield with Different Vectors and Electroporation Apparatus

Figure 3:
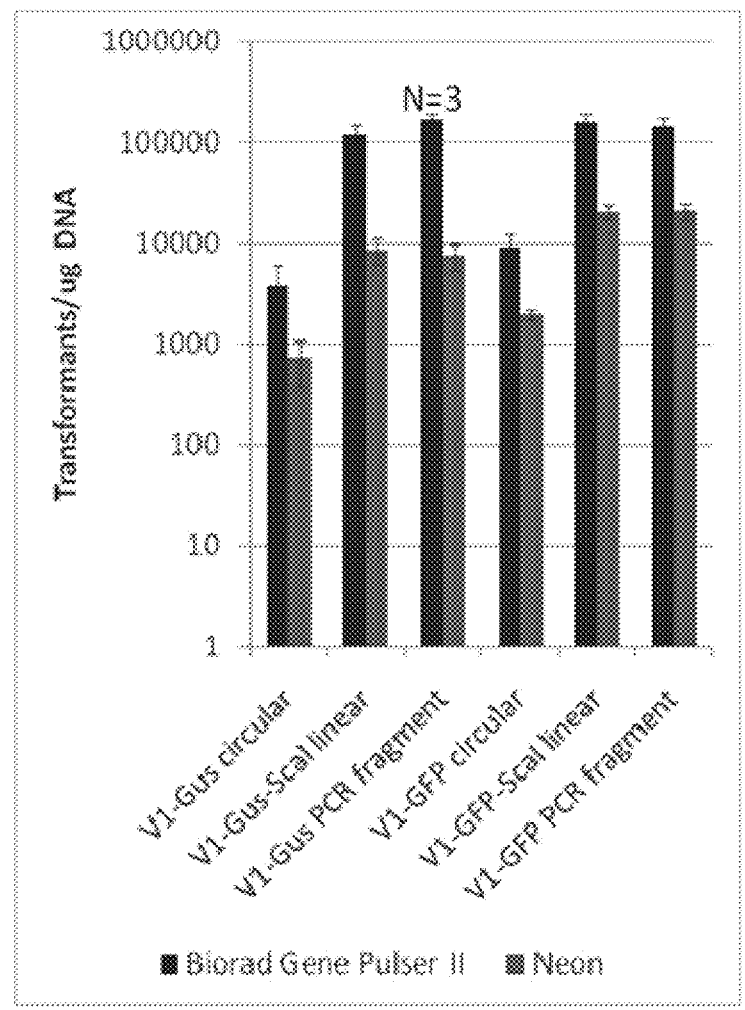
FIG. 3 shows the transformation efficiency when using the optimized transformation buffer with the Bio-Rad Gene Pulser® II and Neon® electroporation devices.

Wild type *Chlamydomonas reinhardtii* cells were washed twice with 2.5 ml of an electroporation buffer comprising 40 mM sucrose, 10 mM sorbitol and 10 mm CHES adjusted to a pH of 9.25. After washing, the cells were resuspended in the electroporation buffer at a concentration of $2 \times 10^8$ cells/ml. For each electroporation reaction, 250 µl cells were mixed with 2 µg of DNA and incubated at 4° C. for 5 min. Immediately before electroporation the reaction mixture was transferred to pre-chilled cuvettes and then electroporation performed in a Bio-Rad Genepulser® II or Neon® apparatus with settings of 500V, 50 mF and 800 W. The reactions were set on the bench for 15 min for resting and then transferred into 10 ml of TAP media with 40 mM sucrose to recover over night with light. Transformation efficiency was determined by plating 1/100 of each reaction. The results are shown in FIG. 3.

We claim:

1. A method for transformation of DNA into an algal cell comprising:
    (a) suspending the algal cells in a buffer, wherein the pH of the buffer is from pH 8 to pH 10,
    (b) adding DNA to be transformed to the algal cell suspension,
    (c) applying an electric pulse to the DNA Algal cell suspension thereby transforming the algal cell with the DNA.
2. The method of claim 1, wherein the buffer comprises one or more sugars and a buffer salt.
3. The method of claim 2, wherein the one or more sugars are selected from the group consisting of sucrose, fructose, maltose, trehalose, sorbitol, maltitol, erythrytol, mannitol, xylose, raffilose and lactose.
4. The method of claim 2, wherein the one or more sugars are sucrose and sorbitol.
5. The method of claim 1, wherein the pH of the buffer is from pH 9 to pH 10.

* * * * *